United States Patent
Xu et al.

(10) Patent No.: US 11,844,490 B2
(45) Date of Patent: Dec. 19, 2023

(54) SUTURE LINKAGE FOR INHIBITING PREMATURE EMBOLIC IMPLANT DEPLOYMENT

(71) Applicant: DePuy Synthes Products, Inc., Raynham, MA (US)

(72) Inventors: Ruijiao Xu, Miami Lakes, FL (US); Lacey Gorochow, Raynham, MA (US)

(73) Assignee: DePuy Synthes Products, Inc., Raynham, MA (US)

( * ) Notice: Subject to any disclaimer, the term of this patent is extended or adjusted under 35 U.S.C. 154(b) by 107 days.

(21) Appl. No.: 17/566,486

(22) Filed: Dec. 30, 2021

(65) Prior Publication Data

US 2023/0210524 A1    Jul. 6, 2023

(51) Int. Cl.
*A61B 17/12* (2006.01)
*A61B 17/04* (2006.01)

(52) U.S. Cl.
CPC .... *A61B 17/0485* (2013.01); *A61B 17/12022* (2013.01); *A61B 2017/0496* (2013.01); *A61B 2017/12054* (2013.01)

(58) Field of Classification Search
CPC ........ A61B 17/12022; A61B 17/12131; A61B 17/1214; A61B 17/12172; A61B 17/12177; A61B 2017/12054; A61F 2/011; A61F 2002/9505; A61F 2002/9511
See application file for complete search history.

(56) References Cited

U.S. PATENT DOCUMENTS

| | | | |
|---|---|---|---|
| 3,429,408 A | 2/1969 | Maker et al. | |
| 5,108,407 A | 4/1992 | Geremia et al. | |
| 5,122,136 A | 6/1992 | Guglielmi et al. | |
| 5,234,437 A | 8/1993 | Sepetka | |

(Continued)

FOREIGN PATENT DOCUMENTS

| | | |
|---|---|---|
| EP | 1985244 A2 | 10/2008 |
| EP | 2498691 | 9/2012 |

(Continued)

OTHER PUBLICATIONS

Extended European Search Report issued in corresponding EP Application No. 22 21 7165 dated Mar. 21, 2023.

*Primary Examiner* — Darwin P Erezo
*Assistant Examiner* — Christian D Knauss
(74) *Attorney, Agent, or Firm* — TROUTMAN PEPPER HAMILTON SANDERS LLP

(57) ABSTRACT

Disclosed herein are various exemplary systems and methods for deploying an implant to a target location of a body vessel. The delivery member can include a tubular body including a lumen and compressed distal portion. The delivery member can include a loop wire with a loop opening positioned approximate the compressed distal portion. The delivery member can include a pull wire that has a proximal pull wire portion and a distal pull wire portion connected by a suture linkage. The suture linkage can include a proximal suture knot engaged to the proximal pull wire portion and a distal suture knot engaged to the distal pull wire portion. Pull wire beads positioned on the proximal pull wire and distal (Continued)

pull wire portion can retain the suture knots during proximal translation of the pull wire. The suture linkage can include slack that is effective to prevent premature deployment of the implant.

20 Claims, 7 Drawing Sheets

(56) References Cited

U.S. PATENT DOCUMENTS

| | | | |
|---|---|---|---|
| 5,250,071 A | 10/1993 | Palermo | |
| 5,263,964 A | 11/1993 | Purdy | |
| 5,334,210 A | 8/1994 | Gianturco | |
| 5,350,397 A | 9/1994 | Palermo et al. | |
| 5,382,259 A | 1/1995 | Phelps et al. | |
| 5,484,409 A | 1/1996 | Atkinson et al. | |
| 5,569,221 A | 10/1996 | Houser et al. | |
| 5,899,935 A | 5/1999 | Ding | |
| 5,925,059 A | 7/1999 | Palermo et al. | |
| 6,113,622 A | 9/2000 | Hieshima | |
| 6,203,547 B1 | 3/2001 | Nguyen et al. | |
| 6,391,037 B1 | 5/2002 | Greenhalgh | |
| 6,454,780 B1 | 9/2002 | Wallace | |
| 6,506,204 B2 | 1/2003 | Mazzocchi | |
| 6,561,988 B1 | 5/2003 | Turturro et al. | |
| 7,367,987 B2 | 5/2008 | Balgobin et al. | |
| 7,371,251 B2 | 5/2008 | Mitelberg et al. | |
| 7,371,252 B2 | 5/2008 | Balgobin et al. | |
| 7,377,932 B2 | 5/2008 | Mitelberg et al. | |
| 7,384,407 B2 | 6/2008 | Rodriguez et al. | |
| 7,708,754 B2 | 5/2010 | Balgobin et al. | |
| 7,708,755 B2 | 5/2010 | Davis, III et al. | |
| 7,799,052 B2 | 9/2010 | Balgobin et al. | |
| 7,811,305 B2 | 10/2010 | Balgobin et al. | |
| 7,819,891 B2 | 10/2010 | Balgobin et al. | |
| 7,819,892 B2 | 10/2010 | Balgobin et al. | |
| 7,901,444 B2 | 3/2011 | Slazas | |
| 7,985,238 B2 * | 7/2011 | Balgobin | A61M 29/00 606/191 |
| 8,062,325 B2 | 11/2011 | Mitelberg et al. | |
| 8,333,796 B2 | 12/2012 | Tompkins et al. | |
| 8,926,650 B2 | 1/2015 | Que et al. | |
| 8,956,381 B2 | 2/2015 | Que et al. | |
| 9,155,540 B2 | 10/2015 | Lorenzo | |
| 9,232,992 B2 | 1/2016 | Heidner | |
| 9,314,326 B2 | 4/2016 | Wallace et al. | |
| 9,532,792 B2 | 1/2017 | Galdonik et al. | |
| 9,532,873 B2 | 1/2017 | Kelley | |
| 9,533,344 B2 | 1/2017 | Monetti et al. | |
| 9,539,011 B2 | 1/2017 | Chen et al. | |
| 9,539,022 B2 | 1/2017 | Bowman | |
| 9,539,122 B2 | 1/2017 | Burke et al. | |
| 9,539,382 B2 | 1/2017 | Nelson | |
| 9,549,830 B2 | 1/2017 | Bruszewski et al. | |
| 9,554,805 B2 | 1/2017 | Tompkins et al. | |
| 9,561,125 B2 | 2/2017 | Bowman et al. | |
| 9,572,982 B2 | 2/2017 | Burnes et al. | |
| 9,579,484 B2 | 2/2017 | Barnell | |
| 9,585,642 B2 | 3/2017 | Dinsmoor et al. | |
| 9,615,832 B2 | 4/2017 | Bose et al. | |
| 9,615,951 B2 | 4/2017 | Bennett et al. | |
| 9,622,753 B2 | 4/2017 | Cox | |
| 9,636,115 B2 | 5/2017 | Henry et al. | |
| 9,636,439 B2 | 5/2017 | Chu et al. | |
| 9,642,675 B2 | 5/2017 | Werneth et al. | |
| 9,655,633 B2 | 5/2017 | Leynov et al. | |
| 9,655,645 B2 | 5/2017 | Staunton | |
| 9,655,989 B2 | 5/2017 | Cruise et al. | |
| 9,662,120 B2 | 5/2017 | Lagodzki et al. | |
| 9,662,129 B2 | 5/2017 | Galdonik et al. | |
| 9,662,238 B2 | 5/2017 | Dwork et al. | |
| 9,662,425 B2 | 5/2017 | Lilja et al. | |
| 9,668,898 B2 | 6/2017 | Wong | |
| 9,675,477 B2 | 6/2017 | Thompson | |
| 9,675,782 B2 | 6/2017 | Connolly | |
| 9,676,022 B2 | 6/2017 | Ensign et al. | |
| 9,692,557 B2 | 6/2017 | Murphy | |
| 9,693,852 B2 | 7/2017 | Lam et al. | |
| 9,700,262 B2 | 7/2017 | Janik et al. | |
| 9,700,399 B2 | 7/2017 | Acosta-Acevedo | |
| 9,717,421 B2 | 8/2017 | Griswold et al. | |
| 9,717,500 B2 | 8/2017 | Tieu et al. | |
| 9,717,502 B2 | 8/2017 | Teoh et al. | |
| 9,724,103 B2 | 8/2017 | Cruise et al. | |
| 9,724,526 B2 | 8/2017 | Strother et al. | |
| 9,750,565 B2 | 9/2017 | Bloom et al. | |
| 9,757,260 B2 | 9/2017 | Greenan | |
| 9,764,111 B2 | 9/2017 | Gulachenski | |
| 9,770,251 B2 | 9/2017 | Bowman et al. | |
| 9,770,577 B2 | 9/2017 | Li et al. | |
| 9,775,621 B2 | 10/2017 | Tompkins et al. | |
| 9,775,706 B2 | 10/2017 | Peterson et al. | |
| 9,775,732 B2 | 10/2017 | Khenansho | |
| 9,788,800 B2 | 10/2017 | Mayoras, Jr. | |
| 9,795,391 B2 | 10/2017 | Saatchi et al. | |
| 9,801,980 B2 | 10/2017 | Karino et al. | |
| 9,808,599 B2 | 11/2017 | Bowman et al. | |
| 9,833,252 B2 | 12/2017 | Sepetka et al. | |
| 9,833,604 B2 | 12/2017 | Lam et al. | |
| 9,833,625 B2 | 12/2017 | Waldhauser et al. | |
| 9,918,718 B2 | 3/2018 | Lorenzo | |
| 10,149,676 B2 | 12/2018 | Mirigian et al. | |
| 10,285,710 B2 | 5/2019 | Lorenzo et al. | |
| 10,292,851 B2 | 5/2019 | Gorochow | |
| 10,420,563 B2 | 9/2019 | Hebert et al. | |
| 10,517,604 B2 | 12/2019 | Bowman et al. | |
| 10,668,258 B1 | 6/2020 | Calhoun et al. | |
| 10,806,402 B2 | 10/2020 | Cadieu et al. | |
| 10,806,461 B2 | 10/2020 | Lorenzo | |
| 2001/0049519 A1 | 12/2001 | Holman et al. | |
| 2002/0072705 A1 | 6/2002 | Vrba et al. | |
| 2002/0165569 A1 | 11/2002 | Ramzipoor et al. | |
| 2003/0009208 A1 | 1/2003 | Snyder et al. | |
| 2004/0034363 A1 | 2/2004 | Wilson et al. | |
| 2004/0059367 A1 | 3/2004 | Davis et al. | |
| 2004/0087964 A1 | 5/2004 | Diaz et al. | |
| 2006/0025801 A1 | 2/2006 | Lulo et al. | |
| 2006/0064151 A1 | 3/2006 | Guterman | |
| 2006/0100687 A1 | 5/2006 | Fahey et al. | |
| 2006/0116711 A1 | 6/2006 | Elliott et al. | |
| 2006/0116714 A1 | 6/2006 | Sepetka et al. | |
| 2006/0135986 A1 | 6/2006 | Wallace et al. | |
| 2006/0206139 A1 | 9/2006 | Tekulve | |
| 2006/0241685 A1 | 10/2006 | Wilson et al. | |
| 2006/0247677 A1 | 11/2006 | Cheng et al. | |
| 2006/0276824 A1 | 12/2006 | Mitelberg et al. | |
| 2006/0276825 A1 | 12/2006 | Mitelberg et al. | |
| 2006/0276826 A1 | 12/2006 | Mitelberg et al. | |
| 2006/0276827 A1 | 12/2006 | Mitelberg et al. | |
| 2006/0276830 A1 | 12/2006 | Balgobin et al. | |
| 2006/0276833 A1 | 12/2006 | Balgobin et al. | |
| 2007/0010850 A1 | 1/2007 | Balgobin et al. | |
| 2007/0055302 A1 | 3/2007 | Henry et al. | |
| 2007/0083132 A1 | 4/2007 | Sharrow | |
| 2007/0233168 A1 | 10/2007 | Davis et al. | |
| 2007/0270903 A1 | 11/2007 | Davis, III et al. | |
| 2008/0027561 A1 | 1/2008 | Mitelberg et al. | |
| 2008/0045997 A1 | 2/2008 | Balgobin et al. | |
| 2008/0097462 A1 | 4/2008 | Mitelberg et al. | |
| 2008/0119887 A1 | 5/2008 | Que et al. | |
| 2008/0269721 A1 | 10/2008 | Balgobin et al. | |
| 2008/0281350 A1 | 11/2008 | Sepetka | |
| 2008/0300616 A1 | 12/2008 | Que et al. | |
| 2008/0306503 A1 | 12/2008 | Que et al. | |
| 2009/0062726 A1 | 3/2009 | Ford et al. | |
| 2009/0099592 A1 | 4/2009 | Buiser et al. | |
| 2009/0312748 A1 | 12/2009 | Johnson et al. | |
| 2010/0094395 A1 | 4/2010 | Kellett | |
| 2010/0114017 A1 | 5/2010 | Lenker et al. | |
| 2010/0206453 A1 | 8/2010 | Leeflang et al. | |
| 2010/0324649 A1 | 12/2010 | Mattsson | |
| 2011/0092997 A1 | 4/2011 | Kang | |
| 2011/0118776 A1 | 5/2011 | Chen et al. | |

(56) References Cited

U.S. PATENT DOCUMENTS

| | | |
|---|---|---|
| 2011/0202085 A1 | 8/2011 | Loganathan et al. |
| 2011/0295303 A1 | 12/2011 | Freudenthal |
| 2012/0035707 A1 | 2/2012 | Mitelberg et al. |
| 2012/0041472 A1 | 2/2012 | Tan et al. |
| 2012/0083868 A1 | 4/2012 | Shrivastava et al. |
| 2012/0172913 A1 | 7/2012 | Kurrus et al. |
| 2012/0172921 A1 | 7/2012 | Yamanaka et al. |
| 2012/0179194 A1 | 7/2012 | Wilson et al. |
| 2012/0283768 A1 | 11/2012 | Cox et al. |
| 2012/0289772 A1 | 11/2012 | O'Connell et al. |
| 2013/0066413 A1 | 3/2013 | Jin et al. |
| 2013/0296915 A1 | 11/2013 | Bodewadt |
| 2013/0325054 A1 | 12/2013 | Watson |
| 2014/0058435 A1 | 2/2014 | Jones et al. |
| 2014/0135812 A1 | 5/2014 | Divino et al. |
| 2014/0200607 A1 | 7/2014 | Sepetka et al. |
| 2014/0243883 A1 | 8/2014 | Tsukashima et al. |
| 2014/0277084 A1 | 9/2014 | Mirigian et al. |
| 2014/0277085 A1 | 9/2014 | Mirigian et al. |
| 2014/0277092 A1 | 9/2014 | Teoh et al. |
| 2014/0277093 A1 | 9/2014 | Guo et al. |
| 2014/0277100 A1 | 9/2014 | Kang |
| 2015/0005808 A1 | 1/2015 | Chouinard et al. |
| 2015/0025562 A1 | 1/2015 | Dinh et al. |
| 2015/0182227 A1 | 7/2015 | Le et al. |
| 2015/0230802 A1 | 8/2015 | Lagodzki et al. |
| 2015/0335333 A1 | 11/2015 | Jones et al. |
| 2016/0008003 A1 | 1/2016 | Kleshinski et al. |
| 2016/0022275 A1 | 1/2016 | Garza |
| 2016/0022445 A1 | 1/2016 | Ruvalcaba et al. |
| 2016/0045347 A1 | 2/2016 | Smouse et al. |
| 2016/0157869 A1 | 6/2016 | Elgård et al. |
| 2016/0228125 A1 | 8/2016 | Pederson, Jr. et al. |
| 2016/0278782 A1 | 9/2016 | Anderson et al. |
| 2016/0310304 A1 | 10/2016 | Mialhe |
| 2016/0331383 A1 | 11/2016 | Hebert et al. |
| 2016/0346508 A1 | 12/2016 | Williams et al. |
| 2017/0007264 A1 | 1/2017 | Cruise et al. |
| 2017/0007265 A1 | 1/2017 | Guo et al. |
| 2017/0020670 A1 | 1/2017 | Murray et al. |
| 2017/0020700 A1 | 1/2017 | Bienvenu et al. |
| 2017/0027640 A1 | 2/2017 | Kunis et al. |
| 2017/0027692 A1 | 2/2017 | Bonhoeffer et al. |
| 2017/0027725 A1 | 2/2017 | Argentine |
| 2017/0035436 A1 | 2/2017 | Morita |
| 2017/0035567 A1 | 2/2017 | Duffy |
| 2017/0042548 A1 | 2/2017 | Lam |
| 2017/0049596 A1 | 2/2017 | Schabert |
| 2017/0071737 A1 | 3/2017 | Kelley |
| 2017/0072452 A1 | 3/2017 | Monetti et al. |
| 2017/0079671 A1 | 3/2017 | Morero et al. |
| 2017/0079680 A1 | 3/2017 | Bowman |
| 2017/0079766 A1 | 3/2017 | Wang et al. |
| 2017/0079767 A1 | 3/2017 | Leon-Yip |
| 2017/0079812 A1 | 3/2017 | Lam et al. |
| 2017/0079817 A1 | 3/2017 | Sepetka et al. |
| 2017/0079819 A1 | 3/2017 | Pung et al. |
| 2017/0079820 A1 | 3/2017 | Lam et al. |
| 2017/0086851 A1 | 3/2017 | Wallace et al. |
| 2017/0086996 A1 | 3/2017 | Peterson et al. |
| 2017/0095258 A1 | 4/2017 | Tassoni et al. |
| 2017/0095259 A1 | 4/2017 | Tompkins et al. |
| 2017/0100126 A1 | 4/2017 | Bowman et al. |
| 2017/0100141 A1 | 4/2017 | Morero et al. |
| 2017/0100143 A1 | 4/2017 | Granfield |
| 2017/0100183 A1 | 4/2017 | Iaizzo et al. |
| 2017/0105739 A1 | 4/2017 | Dias et al. |
| 2017/0113023 A1 | 4/2017 | Steingisser et al. |
| 2017/0147765 A1 | 5/2017 | Mehta |
| 2017/0151032 A1 | 6/2017 | Loisel |
| 2017/0165062 A1 | 6/2017 | Rothstein |
| 2017/0165065 A1 | 6/2017 | Rothstein et al. |
| 2017/0165454 A1 | 6/2017 | Tuohy et al. |
| 2017/0172581 A1 | 6/2017 | Bose et al. |
| 2017/0172766 A1 | 6/2017 | Vong et al. |
| 2017/0172772 A1 | 6/2017 | Khenansho |
| 2017/0189033 A1 | 7/2017 | Sepetka et al. |
| 2017/0189035 A1 | 7/2017 | Porter |
| 2017/0215902 A1 | 8/2017 | Leynov et al. |
| 2017/0216484 A1 | 8/2017 | Cruise et al. |
| 2017/0224350 A1 | 8/2017 | Shimizu et al. |
| 2017/0224355 A1 | 8/2017 | Bowman et al. |
| 2017/0224467 A1 | 8/2017 | Piccagli et al. |
| 2017/0224511 A1 | 8/2017 | Dwork et al. |
| 2017/0224953 A1 | 8/2017 | Tran et al. |
| 2017/0231749 A1 | 8/2017 | Perkins et al. |
| 2017/0245864 A1 | 8/2017 | Franano et al. |
| 2017/0245885 A1 | 8/2017 | Lenker |
| 2017/0252064 A1 | 9/2017 | Staunton |
| 2017/0258476 A1 | 9/2017 | Hayakawa et al. |
| 2017/0265983 A1 | 9/2017 | Lam et al. |
| 2017/0281192 A1 | 10/2017 | Tieu et al. |
| 2017/0281331 A1 | 10/2017 | Perkins et al. |
| 2017/0281344 A1 | 10/2017 | Costello |
| 2017/0281909 A1 | 10/2017 | Northrop et al. |
| 2017/0281912 A1 | 10/2017 | Melder et al. |
| 2017/0290593 A1 | 10/2017 | Cruise et al. |
| 2017/0290654 A1 | 10/2017 | Sethna |
| 2017/0296324 A1 | 10/2017 | Argentine |
| 2017/0296325 A1 | 10/2017 | Marrocco et al. |
| 2017/0303939 A1 | 10/2017 | Greenhalgh et al. |
| 2017/0303942 A1 | 10/2017 | Greenhalgh et al. |
| 2017/0303947 A1 | 10/2017 | Greenhalgh et al. |
| 2017/0303948 A1 | 10/2017 | Wallace et al. |
| 2017/0304041 A1 | 10/2017 | Argentine |
| 2017/0304097 A1 | 10/2017 | Corwin et al. |
| 2017/0304595 A1 | 10/2017 | Nagasrinivasa et al. |
| 2017/0312109 A1 | 11/2017 | Le |
| 2017/0312484 A1 | 11/2017 | Shipley et al. |
| 2017/0316561 A1 | 11/2017 | Helm et al. |
| 2017/0319826 A1 | 11/2017 | Bowman et al. |
| 2017/0333228 A1 | 11/2017 | Orth et al. |
| 2017/0333236 A1 | 11/2017 | Greenan |
| 2017/0333678 A1 | 11/2017 | Bowman et al. |
| 2017/0340383 A1 | 11/2017 | Bloom et al. |
| 2017/0348014 A1 | 12/2017 | Wallace et al. |
| 2017/0348514 A1 | 12/2017 | Guyon et al. |
| 2017/0367712 A1 | 12/2017 | Johnson et al. |
| 2018/0028779 A1 | 2/2018 | von Oepen et al. |
| 2018/0036508 A1 | 2/2018 | Ozasa et al. |
| 2018/0078263 A1 | 3/2018 | Stoppenhagen et al. |
| 2018/0228493 A1 | 8/2018 | Aguilar et al. |
| 2018/0250150 A1 | 9/2018 | Majercak et al. |
| 2018/0280667 A1 | 10/2018 | Keren |
| 2018/0289375 A1 | 10/2018 | Hebert et al. |
| 2018/0296222 A1 | 10/2018 | Hebert et al. |
| 2018/0325706 A1 | 11/2018 | Hebert et al. |
| 2019/0142565 A1 | 5/2019 | Follmer et al. |
| 2019/0159784 A1 | 5/2019 | Sananes et al. |
| 2019/0192162 A1 | 6/2019 | Lorenzo et al. |
| 2019/0231566 A1 | 8/2019 | Tassoni et al. |
| 2019/0255290 A1 | 8/2019 | Snyder et al. |
| 2019/0314033 A1 | 10/2019 | Mirigian et al. |
| 2019/0328398 A1 | 10/2019 | Lorenzo |
| 2020/0138448 A1 | 5/2020 | Dasnurkar et al. |
| 2020/0147347 A1 | 5/2020 | Cottone |
| 2020/0187951 A1 | 6/2020 | Blumenstyk |
| 2020/0229957 A1 | 7/2020 | Bardsley et al. |
| 2020/0397444 A1 | 12/2020 | Montidoro et al. |
| 2021/0001082 A1 | 1/2021 | Lorenzo et al. |
| 2021/0045759 A1 | 2/2021 | Merhi et al. |
| 2021/0085498 A1 | 3/2021 | Nygaard et al. |
| 2021/0186513 A1 | 6/2021 | Hoshino et al. |
| 2021/0196281 A1 | 7/2021 | Blumenstyk et al. |
| 2021/0213252 A1 | 7/2021 | Lorenzo et al. |
| 2021/0338248 A1 | 11/2021 | Lorenzo et al. |
| 2021/0353299 A1 | 11/2021 | Hamel et al. |

FOREIGN PATENT DOCUMENTS

| | | |
|---|---|---|
| EP | 3092956 A1 | 11/2016 |
| EP | 3501427 A1 | 6/2019 |
| EP | 3799803 A1 | 4/2021 |
| EP | 3854321 A1 | 7/2021 |

(56) References Cited

FOREIGN PATENT DOCUMENTS

| | | |
|---|---|---|
| EP | 1188414 A1 | 3/2022 |
| EP | 4119065 A1 | 1/2023 |
| JP | 2006-334408 A | 12/2006 |
| JP | 2012-523943 A | 10/2012 |
| JP | 2013-78584 A | 5/2013 |
| JP | 2014-399 A | 1/2014 |
| WO | 2008064209 A1 | 5/2008 |
| WO | WO 2009/132045 A2 | 10/2009 |
| WO | WO 2012/158152 A1 | 11/2012 |
| WO | WO 2016/014985 A1 | 1/2016 |
| WO | WO 2017/066386 A1 | 4/2017 |
| WO | WO 2018/022186 A1 | 2/2018 |
| WO | WO 2020/148768 A1 | 7/2020 |

* cited by examiner

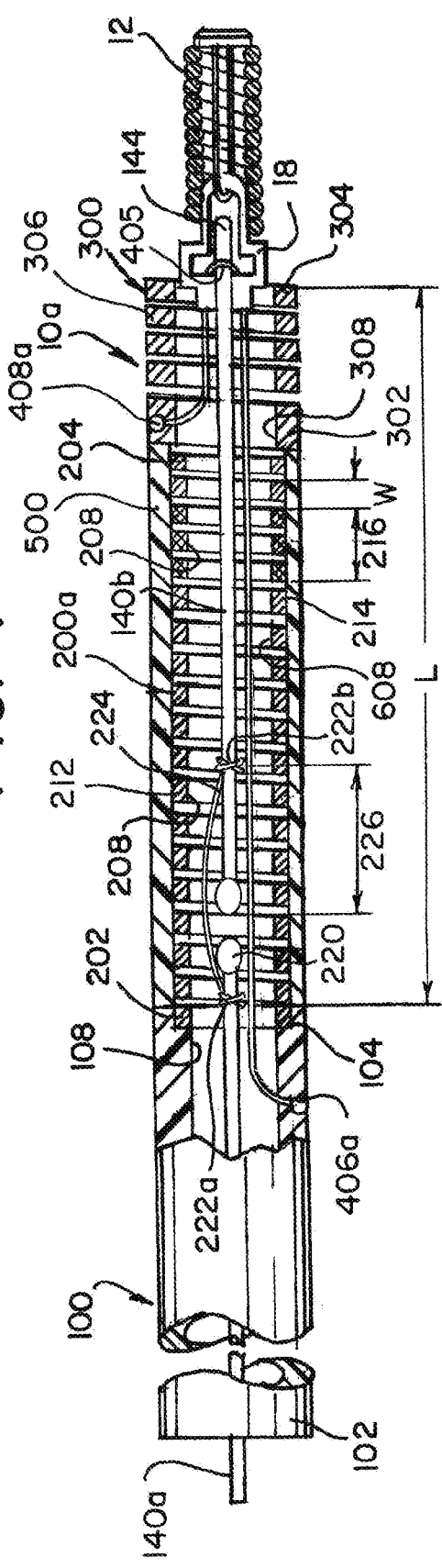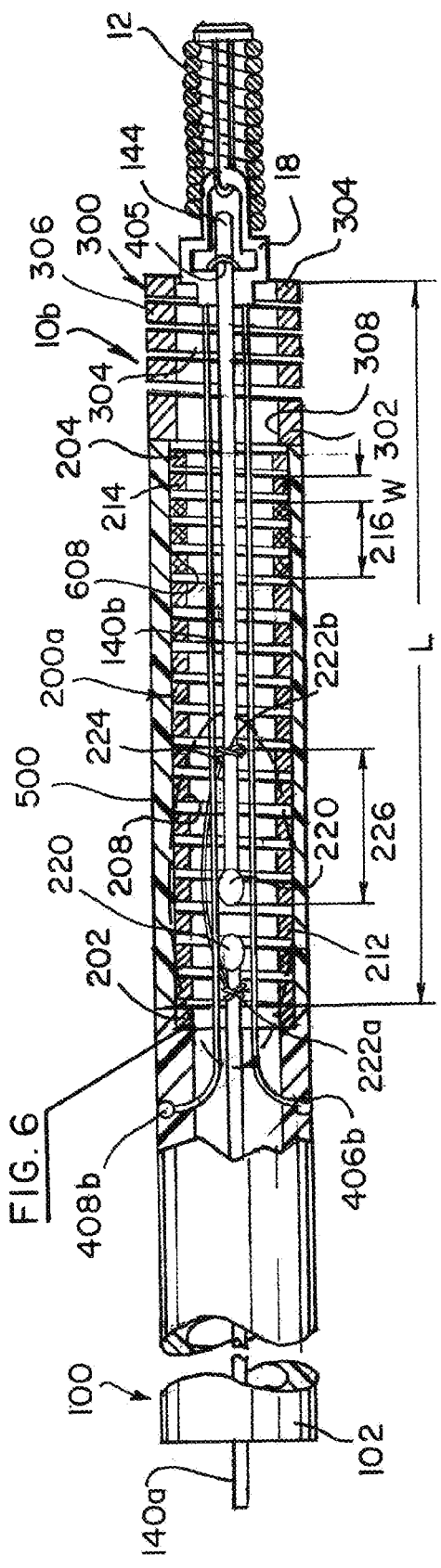

FIG. 3
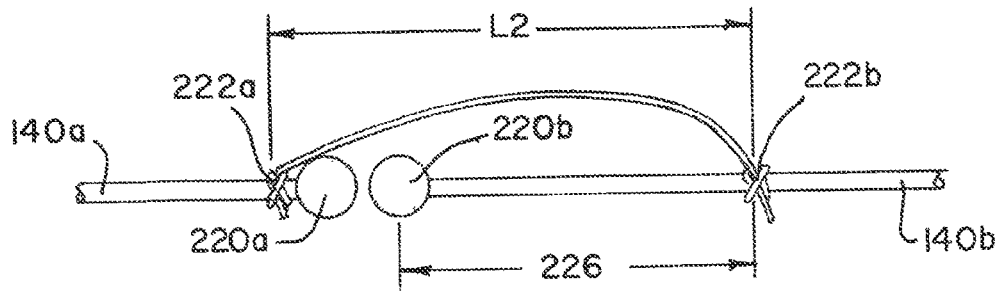
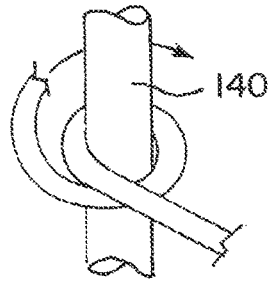
FIG. 4A
STEP 1
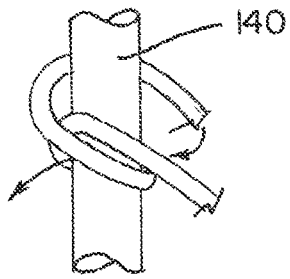
FIG. 4B
STEP 2
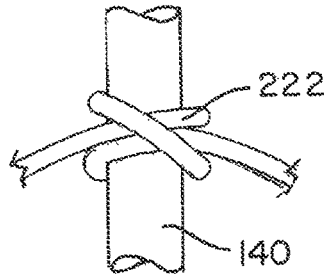
FIG. 4C
STEP 3
FIG. 5A
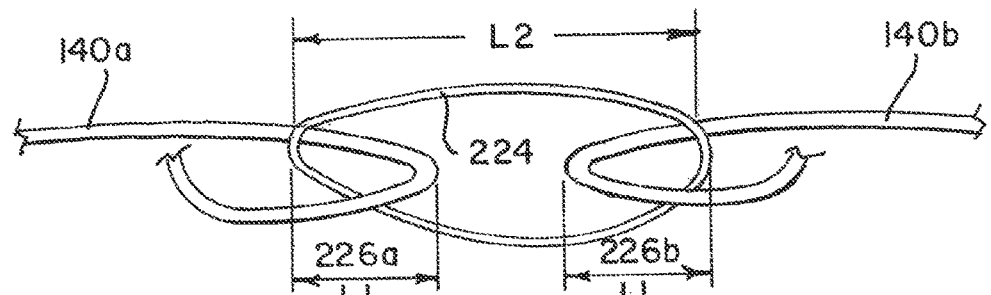
FIG. 5B
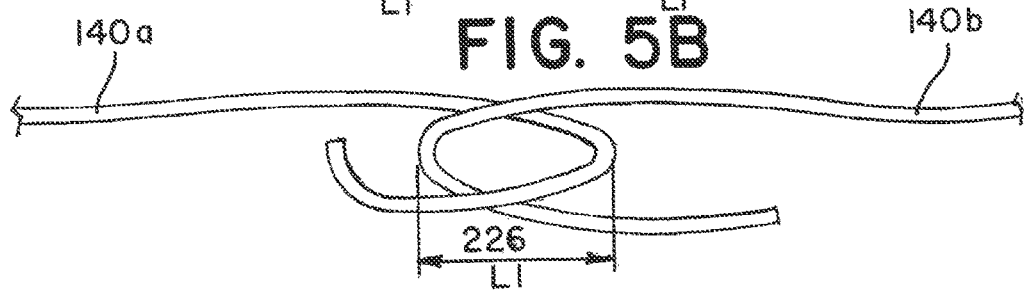
FIG. 7A
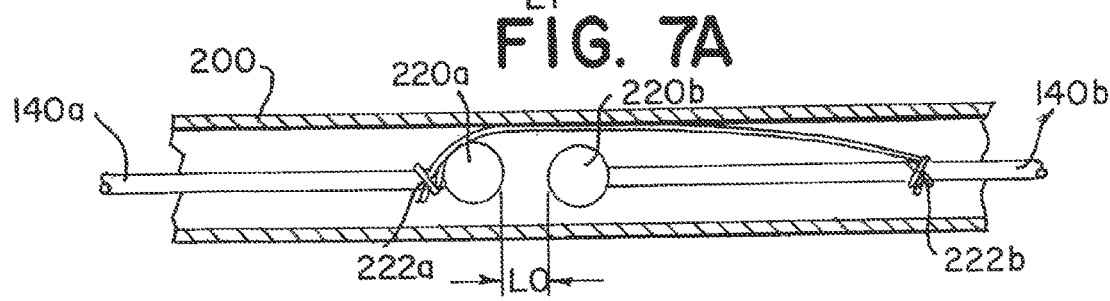

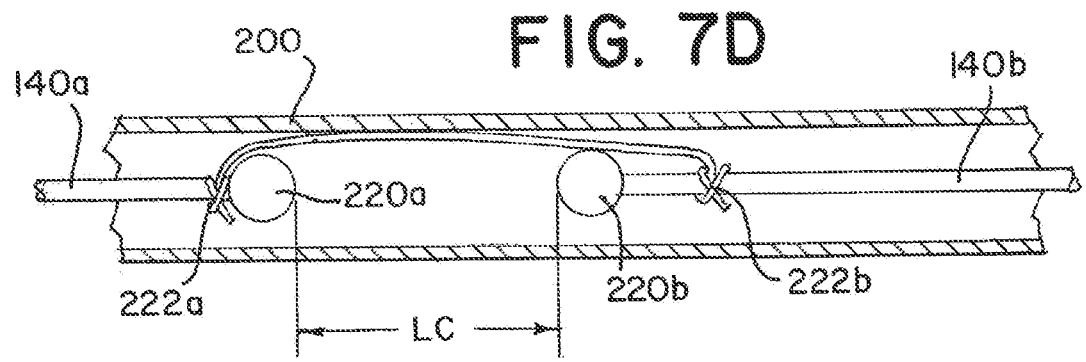
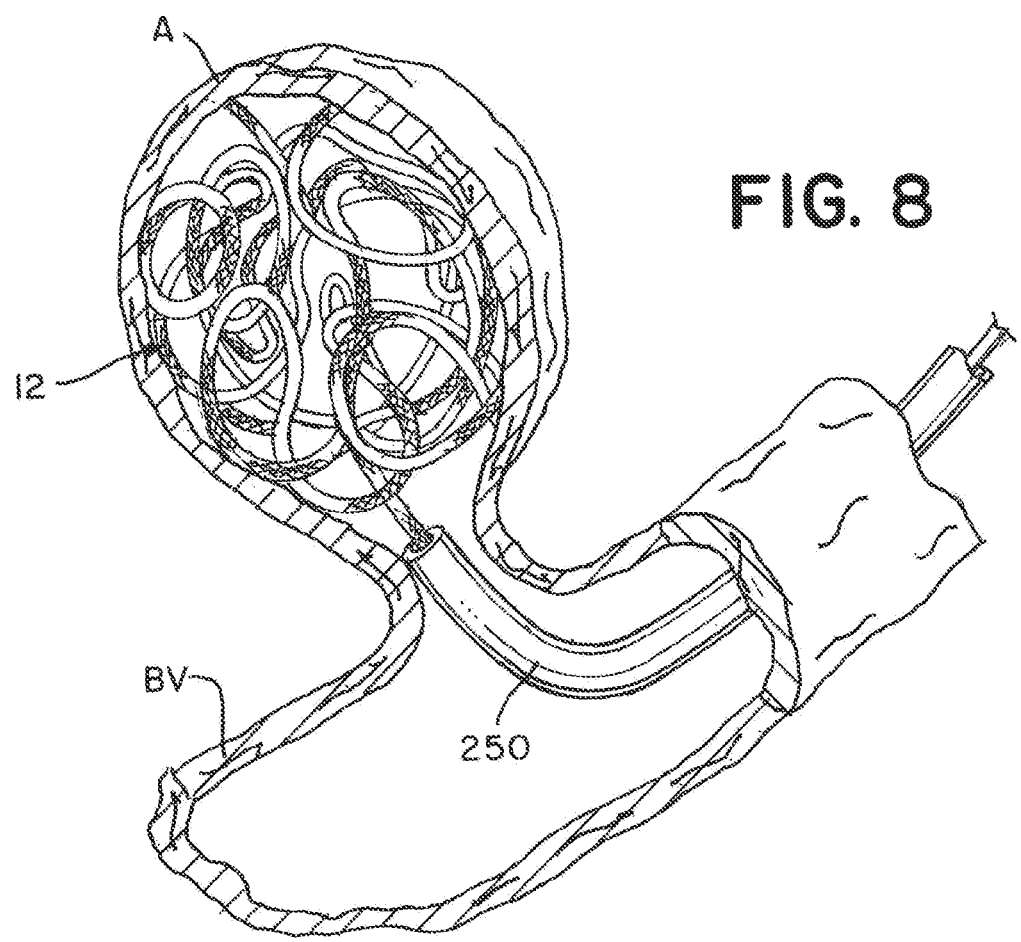

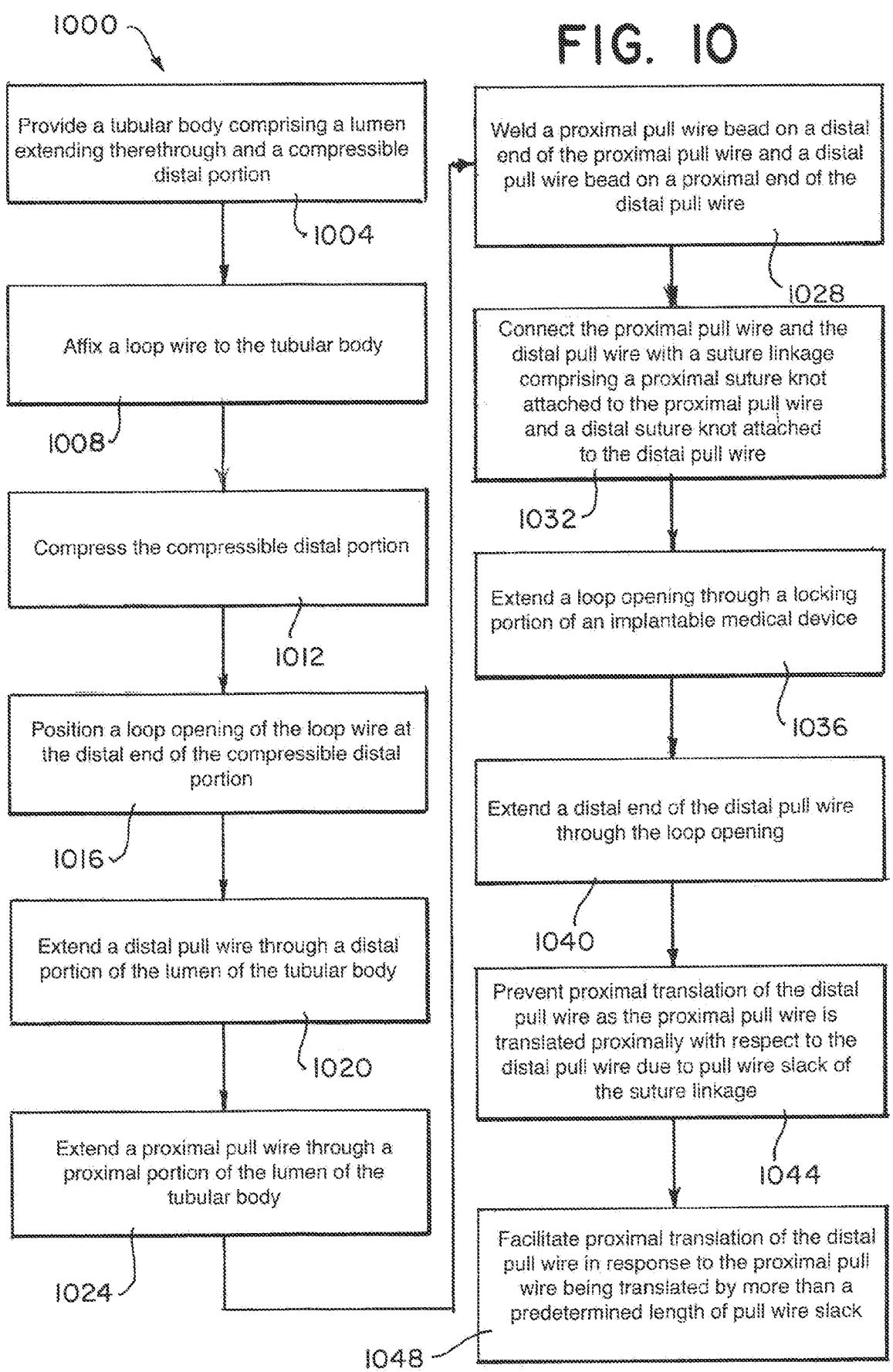

SUTURE LINKAGE FOR INHIBITING PREMATURE EMBOLIC IMPLANT DEPLOYMENT

FIELD OF INVENTION

The present invention relate to aneurysm treatment devices and more particularly, to improved delivery systems for embolic implants that prevent premature implant deployment.

BACKGROUND

Numerous intravascular implant devices are known in the field. Many are deployed mechanically, via systems that combine one or more catheters and wires for delivery. Examples of implants that can be delivered mechanically include embolic elements, stents, grafts, drug delivery implants, flow diverters, filters, stimulation leads, sensing leads, or other implantable structures delivered through a microcatheter. Some obstetric and gastrointestinal implants may also be implanted via similar systems that combine one or more catheters and wires. Devices that may be released or deployed by mechanical means vary greatly in design but can employ a similar delivery catheter and wire system. Many such catheter-based delivery systems include a wire for retention of the implant in the catheter until the time for release of the device. These systems are then actuated by retracting or pulling the wire relative to the catheter. Such a wire is referred to herein as a "pull wire".

One issue with current catheter-based delivery systems is premature detachment of the implantable device. Premature detachment occurs when the implant is detached from the delivery system before reaching the treatment site. This may occur due to the tortuosity experienced by the delivery system as it passes through the vasculature of the patient, which can cause an increase in friction between the "pull wire" and the delivery system causing the pull wire to move proximally while the delivery system is moving distally.

Accordingly, there is a need for an improved implant delivery system that prevents premature detachment of the implant as it is delivered through tortuous vasculature. This disclosure is directed to this and other considerations.

SUMMARY

Disclosed herein are various exemplary systems and methods for deploying an implant to a target location of a body vessel. The delivery member can include a tubular body including a lumen and compressed distal portion. The delivery member can include a loop wire with a loop opening positioned approximate the compressed distal portion. The delivery member can include a pull wire that has a proximal pull wire portion and a distal pull wire portion connected by a suture linkage. The suture linkage can include a proximal suture knot engaged to the proximal pull wire portion and a distal suture knot engaged to the distal pull wire portion. Pull wire beads positioned on the proximal pull wire portion and distal pull wire portion can retain the suture knots during proximal translation of the pull wire. The suture linkage can include slack that is effective to prevent premature deployment of the implant.

In one aspect, a delivery system for deploying an implantable medical device to a target location of a body vessel is disclosed. The delivery system can include a tubular body having a lumen extending therethrough. The tubular body can include a compressed distal portion. The delivery system can include a loop wire having a first end affixed to the tubular body and a loop opening positioned approximate the compressed distal portion. The delivery system can include a pull wire that extends through the lumen. The pull wire can include a proximal pull wire portion, a distal pull wire portion that is separate from the proximal pull wire portion, and a suture linkage that connects the proximal pull wire portion and the distal pull wire portion. The suture linkage can include a proximal suture knot that can be slideably engaged to the proximal pull wire portion and a distal suture knot slideably engaged to the distal pull wire portion.

In some embodiments, a distal end of the proximal pull wire portion can include a proximal pull wire bead and a proximal end of the distal pull wire portion can include a distal pull wire bead. The proximal pull wire bead can be configured to retain the proximal suture knot on the proximal pull wire portion during proximal translation of the proximal pull wire portion. The distal pull wire bead can be configured to retain the distal suture knot on the distal pull wire portion during proximal translation of the pull wire. The loop wire and the distal pull wire portion can be positioned to secure the implantable medical device to the delivery system. The suture linkage can include pull wire slack that facilitates the proximal pull wire portion to be translated proximally with respect to the distal pull wire portion while the distal pull wire portion remains stationary for a predetermined length which causes the distal suture knot to translate proximally to abut the distal pull wire bead such that when the distal suture knot abuts the distal pull wire bead, both the proximal pull wire portion and the distal pull wire portion translate proximally as a unit. The pull wire slack can be effective to inhibit premature deployment of the implantable medical device.

In some embodiments, the loop wire and the pull wire are movable to release the implantable medical device from the delivery system.

In some embodiments, the predetermined length of the pull wire slack is a length between approximately 2 mm and 3 mm. In some embodiments, the suture linkage has a predetermined length that fits within the tubular body of the delivery system.

In some embodiments, the tubular body can include a proximal hypotube, a flexible coil extending from a distal end of the proximal hypotube, and the compressed distal portion can extend from a distal end of the flexible coil. The lumen can extend from a proximal end of the proximal hypotube, through the proximal hypotube, through the flexible coil, through the compressed distal portion, and to a distal end of the compressed distal portion. In some embodiments, a sleeve extends along a majority of the flexible coil.

In some embodiments, upon initial proximal translation of the proximal pull wire portion, the distal pull wire portion remains fixed in position while the distal suture knot slides along the distal pull wire portion for a predetermined length of the pull wire slack. According to some embodiments, the proximal pull wire portion is translated for a distance longer than the predetermined length to deploy the implantable medical device.

In some embodiments, each suture knot is a clove knot adapted to slide against the pull wire when the pull wire is translated proximally.

In some embodiments, the proximal pull wire bead includes a first laser weld forming a diameter larger than a diameter of the proximal suture knot and the distal pull wire bead includes a second laser weld forming a diameter larger than a diameter of the distal suture knot. According to some embodiments the distal suture knot and the proximal suture knot each comprise a clove hitch knot.

In another aspect, a method is disclosed. The method can include providing a tubular body including a lumen extending therethrough and a compressed distal portion. The method can include affixing a loop wire to the tubular body and compressing the compressed distal portion. The method can include positioning a loop opening in the loop wire approximate a distal end of the compressed distal portion while the loop wire is affixed to the tubular body such that the loop wire is extended through the lumen. The method can include extending a distal pull wire portion through a distal portion of the lumen of the tubular body and extending a proximal pull wire portion, separate from the distal pull wire portion, through a proximal portion of the lumen of the tubular body. The method can include connecting the proximal pull wire portion and the distal pull wire portion with a suture linkage. The suture linkage can include a proximal suture knot attached to the proximal pull wire portion and a distal suture knot attached to the distal pull wire portion. The proximal pull wire portion, suture linkage, and distal pull wire portion may form a pull wire. The method can include extending the loop opening through a locking portion of an implantable medical device and extending a distal end of the distal pull wire portion through the loop opening.

According to some embodiments, the method can include preventing proximal translation of the distal pull wire portion as the proximal pull wire portion is translated proximally with respect to the distal pull wire portion due to pull wire slack of the suture linkage, and facilitating proximal translation of the distal pull wire portion in response to the proximal pull wire portion being translated proximally by more than a predetermined length of the pull wire slack.

In some embodiments, the method can include preventing premature deployment of the implantable medical device due to pull wire slack of the suture linkage.

In some embodiments, the method can include moving the loop wire and the distal pull wire portion to release the implantable medical device from the delivery system.

In some embodiments, the method can include welding a proximal pull wire bead on a distal end of the proximal pull wire portion and welding a distal pull wire bead on a proximal end of the distal pull wire portion. The method can include following proximal translation of the proximal pull wire portion by more than the predetermined length of the pull wire slack, causing the distal suture knot to abut the distal pull wire bead thereby causing the distal pull wire portion and the proximal pull wire portion to translate proximally as a unit.

In some embodiments, the method can include constructing the tubular body by joining a flexible coil between a proximal hypotube and distal hypotube which includes the compressed distal portion such that the lumen extends from a proximal end of the proximal hypotube through the proximal hypotube, through the flexible coil, through the compressed distal portion, and to a distal end of the compressed distal portion and such that the flexible coil is inhibited from elongating.

According to some embodiments, upon initial proximal translation of the proximal pull wire portion, the distal pull wire portion remains in position while the distal suture knot slides along the distal pull wire portion for the predetermined length of the pull wire slack.

According to some embodiments, the method can include translating the proximal pull wire portion proximally for a distance longer than the predetermined length, thereby deploying the implantable medical device.

BRIEF DESCRIPTION OF THE DRAWINGS

The above and further aspects of this invention are further discussed with reference to the following description in conjunction with the accompanying drawings, in which like numerals indicate like structural elements and features in various figures. The drawings are not necessarily to scale, emphasis instead being placed upon illustrating principles of the invention. The figures depict one or more implementations of the inventive devices, by way of example only, not by way of limitation.

FIG. 1 an illustration of a delivery system and implant, according to aspects of the present invention.

FIG. 2 is an illustration of another delivery system and implant, according to aspects of the present invention.

FIG. 3 is an illustration of a suture linkage, according to aspects of the present invention.

FIGS. 4A-4C are time-sequenced illustrations of forming a clove hitch knot, according to aspects of the present invention.

FIGS. 5A-5B are illustrations of alternate pull wire linkages, according to aspects of the present invention.

FIGS. 7A-7D are illustrations of a proximal pull wire and a distal pull wire joined by a suture linkage such as illustrated in FIGS. 1-3 when the delivery system is navigated through turns in a body lumen such as illustrated in FIG. 6 according to aspects of the present invention.

FIG. 8 is an illustration of embolic coils being positioned within an aneurysm according to aspects of the present invention.

FIG. 10 is a flowchart of an example method of using the delivery member, according to aspects of the present invention.

DETAILED DESCRIPTION

Figure 6:
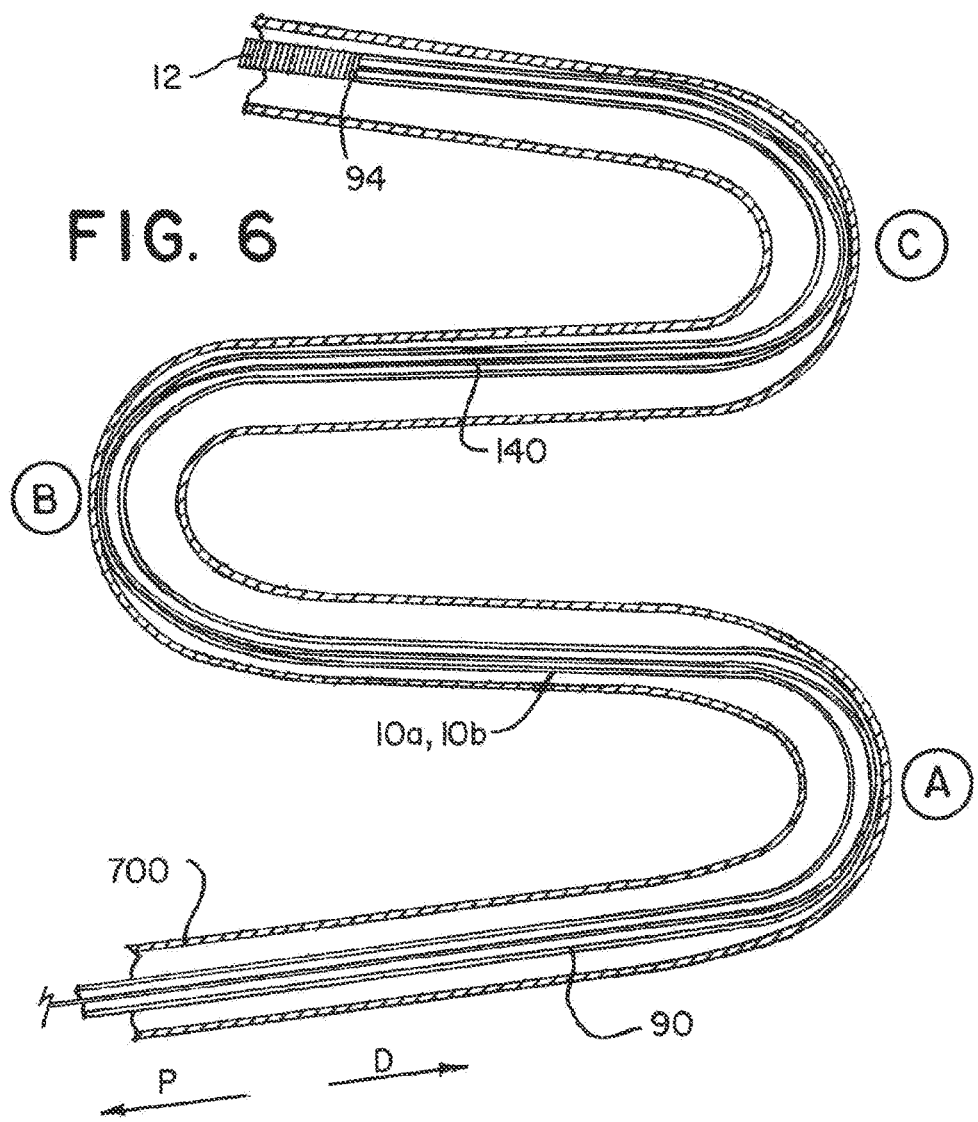
FIG. 6 is an illustration of a delivery system navigating a body lumen according to aspects of the present invention.

The following description of certain examples of the invention should not be used to limit the scope of the present invention. The drawings, which are not necessarily to scale, depict selected embodiments and are not intended to limit the scope of the invention. The detailed description illustrates by way of example, not by way of limitation, the principles of the invention. Other examples, features, aspects, embodiments, and advantages of the invention will become apparent to those skilled in the pertinent art from the following description, which is by way of illustration, one of the best modes contemplated for carrying out the invention. As will be realized, the invention is capable of other different or equivalent aspects, all without departing from the invention. Accordingly, the drawings and descriptions should be regarded as illustrative in nature and not restrictive.

Any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those skilled in the pertinent art in view of the teachings herein. Such modifications and variations are intended to be included within the scope of the claims.

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±10% of the recited value, e.g. "about 90%" may refer to the range of values from 81% to 99%. In addition, as used herein, the terms "patient," "host," "user," and "subject" refer to any human or animal subject and are not intended to limit the systems or methods to human use, although use of the subject invention in a human patient represents a preferred embodiment.

Turning to the figures, as illustrated in FIGS. 1 and 2 an example delivery member 10, 10b, can include a proximal tube 100, a coiled section 200a, a distal tube 300, a sleeve 500 surrounding the coiled section, and a loop wire 400a, 400b, extending through the coiled section 200a. The delivery member 10a, 10b can have a lumen 608 therethrough extending through the proximal tube 100, coiled section 200a, and distal tube 300. That is, the proximal tube 100 can have a lumen 108 therethrough, the coiled section 200a can have a lumen 208 therethrough, the distal tube 300 can have a lumen 308 therethrough, and the lumens 108, 208, 308 can be contiguous to form the lumen 608 through the delivery member 10a, 10b. The proximal tube 100 can have a distal end 104 connected to a proximal end 202 of the coiled section 200a and a distal end 204 of the coiled section 200a can be connected to a proximal end 302 of the distal tube 300.

The distal tube 300 can include a compressible portion 306. The compressible portion 306 can be axially adjustable between an elongated condition and a compressed condition. The compressible portion 306 can be formed from a spiral-cut portion of the tube 300, formed by a laser cutting operation. Additionally, or alternatively, the compressible portion can be formed of a wound wire, spiral ribbon, or other arrangement allowing axial adjustment according to the present invention. Preferably, compressible portion 306 is in the elongated condition at rest and automatically or resiliently returns to the elongated condition from a compressed condition, unless otherwise constrained.

When the delivery member 10a, 10b, is assembled, the coiled section 200a and sleeve 500 can be more flexible than the distal hypotube and the proximal hypotube. One way to measure flexibility is to perform a three-point bend test wherein a portion of the delivery member 10a, 10b is held fixed at two end points, a force is applied perpendicularly to the member 10a, 10b centrally between the points, and flexibility is quantified by the length of deflection of the delivery member 10a, 10b caused by the force. When measured in this way, in some examples, the coiled section 200a and sleeve can be about 1.5 times more flexible than the distal hypotube and about 20 times more flexible than the proximal hypotube 100. That is, when the three-point test is performed identically on the three sections 100, 200a, and 300, the coiled section deflect over a length that is about 1.5 times the deflection of the distal hypotube and about 20 times the length of deflection of the proximal hypotube. Flexibility can be measured in other ways as would be appreciated and understood by a person having pertinent skill in the requisite art. When the delivery member 10a, 10b is assembled, the coiled section 200a and sleeve 500 can be more flexible than the distal hypotube and the proximal hypotube as flexibility is determined by other means as would be known to a person of ordinary skill in the art.

The coiled section can be formed primarily of a non-radiopaque material such as steel and can include a radiopaque section 216 made of a radiopaque material such as platinum and/or tungsten. The radiopaque section 216 can be positioned between a proximal, non-radiopaque section of the coil 212, and a distal, non-radiopaque section of the coil 214. The radiopaque section 216 can be positioned a predetermined distance from a distal end 304 of the delivery member 10a, 10b so that a physician can readily visualize the placement of the distal portion of the delivery member during a treatment procedure. The proximal section 212, radiopaque section 216, and distal section 214 can be concentrically welded.

Delivery members 10a, 10b manufactured according to the illustrations in FIG. 1 and FIG. 2 are demonstrated to have a flexibility of about 25% to about 40% greater than competing delivery systems.

Comparing the delivery member 10a illustrated in FIG. 1 to the delivery member 10b illustrated in FIG. 2, in FIG. 1, the loop wire 400a is illustrated as having a first end attachment 406a to the proximal tube 100 and a second end attachment 408a to the distal tube 300 while, in FIG. 2, the loop wire 400b is illustrated as having a first and second end attachment 406b, 408b both to the proximal tube 100. Although several factors can contribute to the flexibility of the delivery member, all else being equal, the delivery member 10a illustrated in FIG. 1 can be more flexible compared to the delivery member 10b illustrated in FIG. 2 because the delivery member 10a illustrated in FIG. 1 has a single leg of loop wire 400a passing through the coiled section 200a and therefore less material passing through the coiled section 200a compared to the delivery member 10b of FIG. 2, which has two legs of the loop wire 400b passing through the coiled section 200a. Alternative configurations are also contemplated, for instance the loop wire need not have two separable ends, e.g., the legs of the loop wire can be fused, twisted, or otherwise formed as a single unit.

With respect to FIGS. 1 and 2, both delivery member 10a, 10b can include a proximal pull wire 140a and a distal pull wire 140b. The proximal pull wire 140a and distal pull wire 140b can be connected with a suture linkage 224, where the proximal pull wire 140a and distal pull wire 140b are otherwise separate and not connected. The suture linkage 224 can include a proximal suture knot 222a that is attached to the proximal pull wire 140a and a distal suture knot 222b that is attached to the distal pull wire 140b (collectively, suture knots 222). On a distal end of proximal pull wire 140a can be disposed a pull wire bead 220a. Similarly, on a proximal end of distal pull wire 140b can be disposed a pull wire bead 220b (collectively pull wire beads 220). The pull wire beads 220 can have a diameter larger than a diameter of the suture knots 222. Accordingly, pull wire beads 220 can be effective to retain suture knots on the pull wires 140a, 140b. As the delivery member 10a, 10b is delivered to a treatment site through tortuous vasculature of a patient, pull wire 140a can drift proximally in relation to tubular body 90 of delivery member 10a, 10b. Pull wire slack 226 is a distance between distal suture knot 222b and the distal pull wire bead 220b. As the delivery member 10a, 10b is pushed distally towards the treatment site, the pull wire slack 226 is effective to prevent premature deployment of implant 12 from delivery member 10a, 10b by preventing proximal drift of proximal pull wire 140a from affecting distal pull wire 140b until proximal pull wire 140a has been translated proximally by a distance L, which can be an overall length of pull wire slack 226. According to some embodiments, and as discussed in more detail with respect to FIGS. 5A-5B, suture linkage 224 can be provided in a variety of configurations. For example, rather than attaching suture linkage to pull wires 140a, 140b with respective knots, suture linkage 224 can be a loop that is looped around pull wires 140a, 140b. In another embodiment, pull wires 140a, 140b can be looped around each other directly without a suture linkage. Pull wires 140a, 140b can be constructed out of any suitable material, for example stainless steel or memory shape material, such as nitinol. According to some embodiments, pull wires 140a, 140b can be coated with polytetrafluoroethylene (PTFE).

FIG. 3 shows an exemplary suture linkage connecting pull wires 140a, 140b, according to aspects of the present invention. As shown, suture linkage 224 can have an overall length L2 measured from distal suture knot 222b and proximal suture knot 222a. Pull wire slack 226 can have an overall length L1 that can be measured from distal suture knot 222b and distal pull wire bead 220b.

FIGS. 4A-4C shows a time sequence of an exemplary method of forming suture knots 222. According to some embodiments, suture knots can be provided as clove hitch knots. Clove hitch knots is a type of knot that is particularly useful when the position of the knot needs to be adjustable, because a clove hitch knot will loosen when slack is fed towards the knot from either direction. Accordingly a clove hitch knot can be movable along an object the clove knot is tied around. In FIG. 4A the first step of tying a clove hitch knot is shown. First, a free end of a rope is passed around a post the knot is to be attached to. In FIG. 4B, the second step is shown of crossing over the tied end of the rope and crossing over the post. FIG. 4C shows the working end of the rope being slipped under the wrap made in the second step, shown in FIG. 4B, thereby completing the clove hitch knot.

FIGS. 5A-5B are illustrations of alternate pull wire linkages, according to aspects of the present invention. FIG. 5A shows an alternative suture linkage. Rather than being characterized by pull wire beads 220, in this embodiment both distal end of pull wire 140a and proximal end of pull wire 140b have a "J" shaped hooked end around which a suture linkage loop 224 of length L2 can be secured. In this configuration, pull wire slack 226 is formed of pull wire slack 226a, which is a distance between the most proximal end of suture linkage 224 and the most distal end of the "J" hook of pull wire 140a, and pull wire slack 226b, which is a distance between the most distal end of suture linkage 224 and the most proximal end of the "J" hook of pull wire 140b. Accordingly, in this configuration, the pull wire slack 226 is a sum of the lengths of pull wire slack 226a and pull wire slack 226b.

FIG. 5B shows an alternative configuration of pull wires 140a, 140b. In this configuration, both the distal end of pull wire 140a and the proximal end of pull wire 140b have a "J" shaped hooked end which are wrapped around each other. That is, the distal end of pull wire 140a and the proximal end of distal pull wire 140b can directly interface with each other. In this configuration, the pull wire slack 226 can have a length L1 that is measured between the most distal point of pull wire 140a to the most proximal point of wire 140b. The pull wire slack can be understood as the length L1 that the proximal pull wire 140a must be pulled before the distal pull wire 140b begins to translate proximally with the proximal pull wire 140a as a single unit.

FIG. 6 illustrates positioning of an implant 12 such as an embolic coil suitable for aneurysm treatment, a guide catheter 700, and a delivery system 10 including a tubular body 90 and a pull wire 140 within tortuous vasculature (vasculature not illustrated). At bends A, B, and C, the body 90 can extend to a sidewall of the guide catheter 700 on each outer curve of each bend, and likewise, the pull wire 140 can extend to a sidewall of the body 90 on each outer curve of each bend. During a procedure, the tubular body 90 and pull wire 140 can be fed into the guide catheter 700 in the distal direction D, first passing through bend A, then bend B, and then bend C. As the body 90 and pull wire 140 navigate the bends, the distal suture knot 222b may slide proximally along distal pull wire 140b by a distance less than pull wire slack 226 length L1. The pull wire slack can prevent the proximal translation in a proximal direction P of distal pull wire 140b with respect to the tubular body 90 of the delivery member 10a, 10b, which prevents the premature detachment of implant 12 from the delivery member 10a, 10b.

Figure 7B:
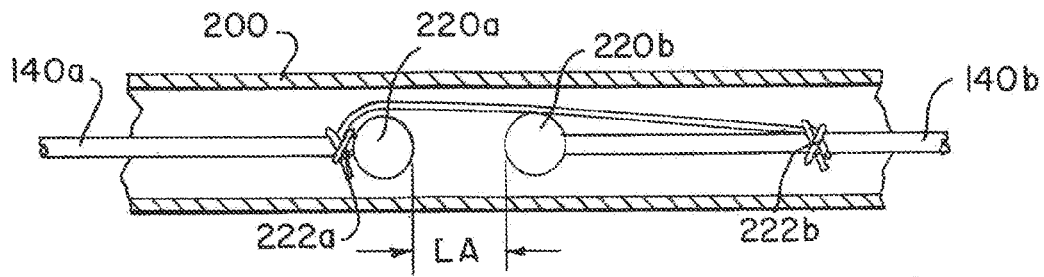
Figure 7C:
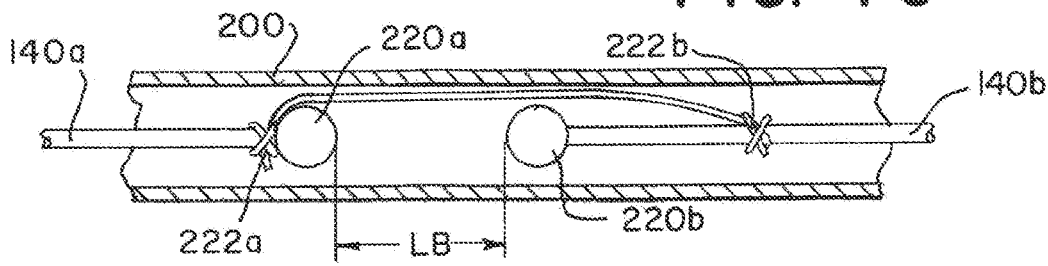

FIGS. 7A through 7D illustrate the progressive movement of the suture linkage 224 as the delivery system 10a,10b moves distally through bends A, B, and C of FIG. 6. FIG. 7A illustrates the positioning of the suture linkage 224 as the distal end 94 of the tubular body approaches bend A. FIG. 7B illustrates the proximal movement of proximal pull wire portion 140a, which increases the gap between proximal pull wire 140a and distal pull wire 140b as the distal end 94 of the tubular body of delivery member 10a, 10b rounds bend A and approaches bend B. FIG. 7C illustrates the proximal pull wire 140a moving further proximally with respect to the tubular body 90 of delivery member 10a, 10b, which increases the gap between proximal pull wire 140a and distal pull 140b, caused by the gradual proximal slide of distal suture knot 222b towards distal pull wire bead 220b as distal end 94 of the tubular body 90 of delivery member 10a, 10b rounds bend B and approaches bend C. FIG. 7D illustrates the moment before distal suture knot 222b engages to distal pull wire bead 220b as the distal end 94 of the tubular body 90 of delivery member 10a, 10b rounds bend C and approaches a treatment site.

Referring collectively to the illustrations in FIGS. 6 and 7A through 7D, as the delivery member 10a, 10b is moved, as the delivery member 10a, 10b is moved distally to a treatment site, the distal suture knot 222b can be free to move in the proximal and distal direction in relation to the tubular body 90. As illustrated, distal suture knot 222b can approach the distal pull wire bead 220b as the delivery member 10a, 10b is moved distally to a treatment site. Arrows illustrated in FIGS. 7A through 7D indicate the proximal movement of the proximal pull wire 140a.

A gap L0, LA, LB, LC between proximal pull wire 140a and distal pull wire 140b can become progressively larger as illustrated in FIGS. 7A through 7D as the delivery system 10a, 10b is moved distally. In FIG. 7B, proximal suture knot 222a abuts proximal pull wire bead 220a, after which point further proximal translation of the proximal pull wire 140a causes distal suture knot 222b to slide along distal pull wire, gradually reducing the distance between distal suture knot 222b and distal pull wire bead 220b.

As shown in FIGS. 7A-7D, proximal pull wire bead 220a may have a diameter D1 and distal pull wire bead 220b may have a diameter D2. According to some embodiments, diameter D1 and diameter D2 may collectively be larger than a diameter of lumen 608 extending through delivery system 10a, 10b. Accordingly, distal pull wire bead 220b can be prevented from sliding past proximal pull wire bead 220a as the delivery system 10a, 10b is delivered through tortuous vasculature to a treatment site, as shown in FIG. 6. Similarly, proximal pull wire bead 220a can be prevented from sliding past distal pull wire bead 220b as the delivery system 10a, 10b is delivered through tortuous vasculature to a treatment site.

Referring back to FIGS. 1-2, the delivery member 10a, 10b can include pull wire slack 226 that is measurable between the distal suture knot 222b and the distal pull wire bead 220b. The pull wire slack 226 can be of length L such that the distal suture knot 222b is unlikely to engage the distal pull wire bead 220b as the delivery member 10a, 10b is delivered to a treatment site. A larger length L of pull wire slack 226 can allow for greater strain relief at the distal end of the distal pull wire 140b, thereby reducing the likelihood of premature deployment of a treatment device. The maximum length of pull wire slack 226 can be limited by ease of manipulation of the proximal end of the delivery member 10a, 10b. For example, it may be difficult for a physician to manipulate a delivery member having an assembly such as illustrated in FIG. 2 that is several inches long. The length L of pull wire slack 226 can therefore be sized to sufficiently relieve strain on the distal end of the distal pull wire 140 to sufficiently reduce the likelihood of premature deployment of a treatment device and also to facilitate ease of manipulation of the delivery member during a treatment procedure. According to some embodiments, the length L of pull wire slack 226 can be a length between approximately 2 mm and approximately 3 mm.

FIG. 8 is an illustration of embolic implant 12 being delivered through catheter 250 and positioned within an aneurysm A on a blood vessel BV. The implant can loop and bend with the aneurysm sac to form a thrombotic mass. The implant can loop back on themselves and/or loop next to other implants. As the aneurysm A becomes increasingly packed, overlapping portions of the implant 12 can press into each other.

Figure 9A:
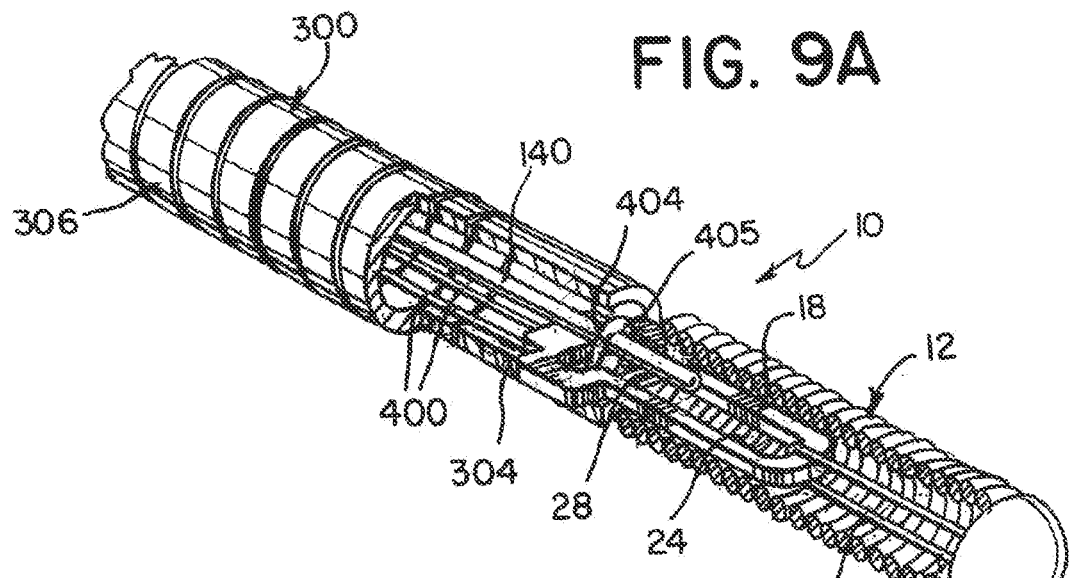
FIGS. 9A-9E illustrate a sequence of steps for releasing an embolic implant from the delivery member, according to aspects of the present invention.
Figure 9B:
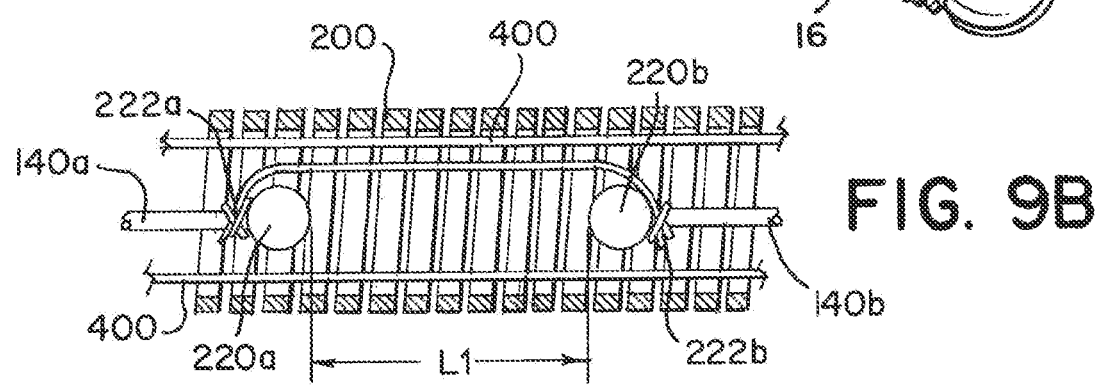
Figure 9C:
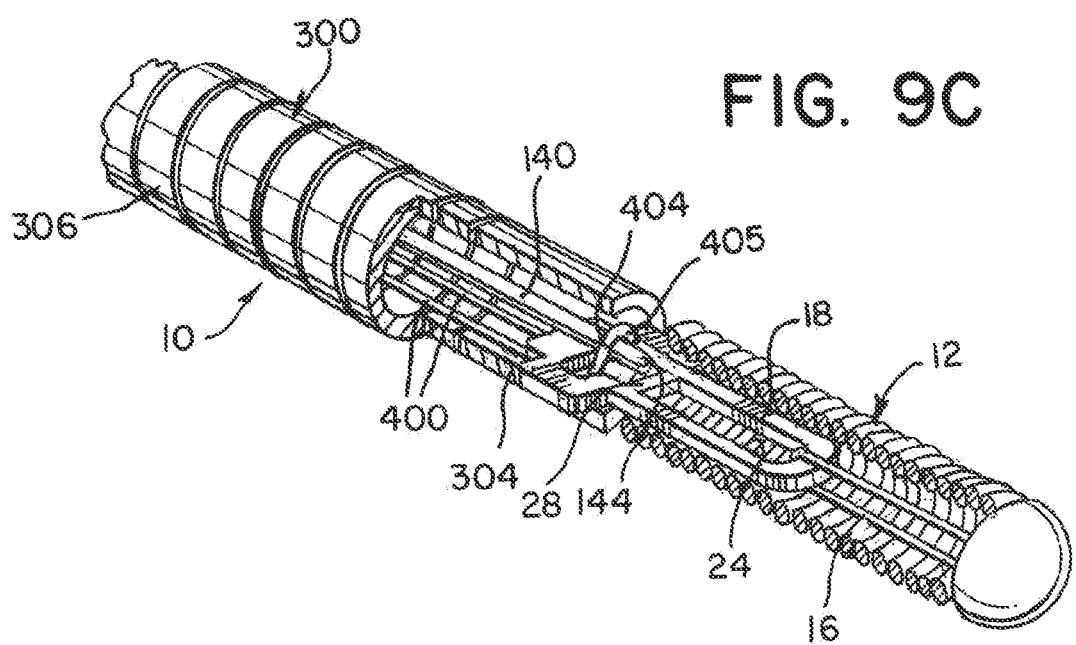
Figure 9D:
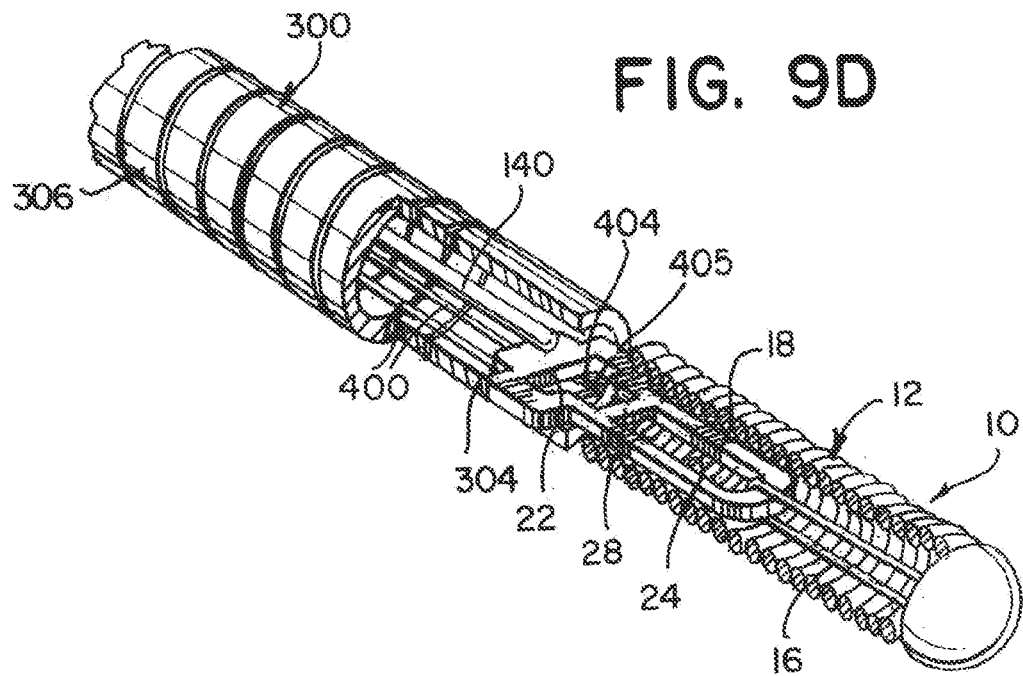
Figure 9E:
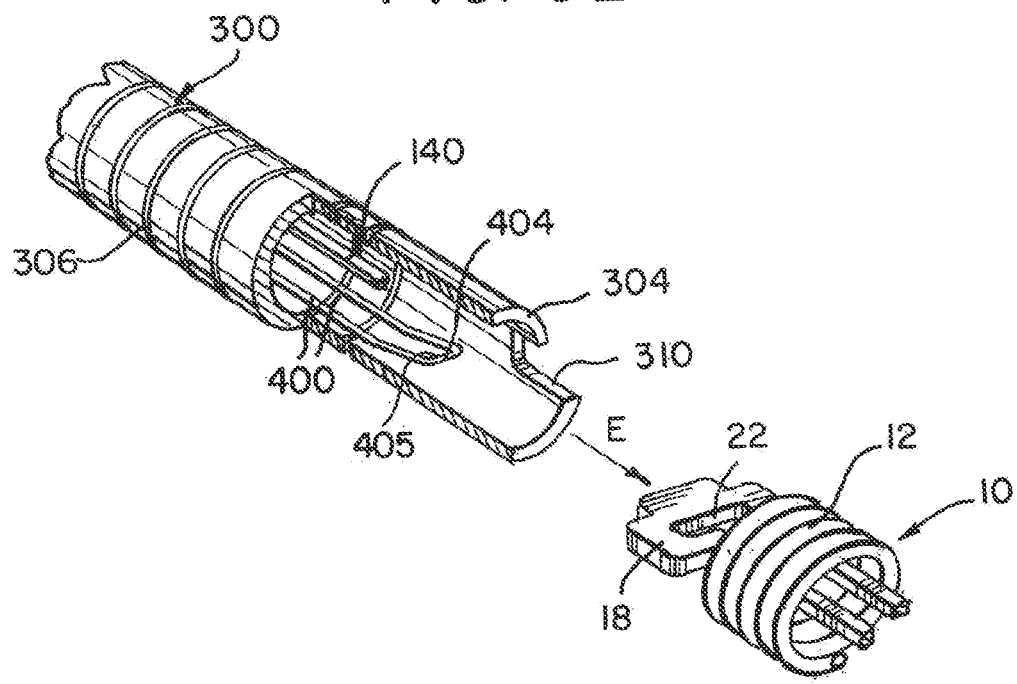

FIGS. 9A-9E illustrate a time sequence of steps for releasing an embolic implant 12 from a delivery member 10. The delivery member 10 can be configured such as illustrated in the previous figures and as otherwise described herein. FIG. 9A illustrates an engagement system including the loop wire 400 and distal pull wire 140b locked into a locking portion 18 of the medical device 12. The compressible portion 306 of the distal tube 300 can be compressed and the loop wire 400 opening 405 at a distal end 404 of the loop wire 400 can be placed through the locking portion 18. When the distal pull wire 140b is put through the opening 405 the medical device 12 is now secure. FIG. 9B illustrates the predetermined length L1 of the pull wire slack 226 that prevents premature detachment of implant 12 as delivery member 10a, 10b travels through the vasculature to a treatment site. As shown, pull wire slack 226 has been completely drawn tight, and further proximal translation of proximal pull wire 140a will cause proximal translation of distal pull wire 140b, thereby releasing implant 12 at a treatment site. FIG. 9C illustrates the distal pull wire 140b being drawn proximally to begin the release sequence for the medical device 12. FIG. 9D illustrates the instant the distal end 144 of the pull wire exits the opening 405 and the pull wire 140 is pulled free of the loop wire 400. The distal end 404 of the loop wire 400 falls away and exits the locking portion 18. As can be seen, there is now nothing holding the medical device 12 to the detachment system 10. FIG. 9E illustrates the end of the release sequence. Here, the compressible portion 306 has extended/returned to its original shape and "sprung" forward. An elastic force E is imparted by the distal end 305 of the distal tube 300 to the implant 12 to "push" it away to ensure a clean separation and delivery of the implant 12.

The compressible portion 306 can have a difference in length (distance of compression) when measured in the compressed configuration and the original, uncompressed configuration of about 0.5 mm to about 0.75 mm. Greater elastic force E can be achieved by using a greater distance of compression. The distance of compression can be determined by the sizing of the loop wire 400, the shape of the locking portion 18, and the shape of the distal end 304 of the distal tube 300.

FIG. 10 is a flowchart of an example method of using the delivery member, according to aspects of the present invention. In block 1004, the method can include providing a tubular body 90. Tubular body 90 includes a lumen 608 extending therethrough and a compressed distal portion 300. The method continues in block 1008 by affixing a loop wire 400a, 400b to the tubular body 90. As shown in FIGS. 1-2, loop wire ends 406, 408 can be attached in a variety of configurations. In one configuration, as shown in FIG. 1, loop wire end 406a is attached to a proximal tube 100 and loop wire end 408a is attached to a compressed distal portion 300. In another configuration, as shown in FIG. 2, loop wire end 406b and 408b are both attached to proximal tube 100. In block 1012, the method can include compressing the compressible distal portion 300. In block 1016, the loop opening 305 of the loop wire 400 can be positioned proximate the distal end 306 of the compressible distal portion 300. In block 1020 the method includes extending a distal pull wire 140b through a distal portion of the lumen 608 of the tubular body 90. In block 1024, the method can include extending a proximal pull wire 140a through a proximal portion of the lumen 608 of the tubular body 90.

In optional block 1028, the method can include welding a proximal pull wire bead 220a on a distal end of the proximal pull wire 140a and a distal pull wire bead 220b on a proximal end of the distal pull wire 140b. In some embodiments, a hooked "J" can be provided on distal end of proximal pull wire 140a and a proximal end of distal pull wire 140b in lieu of pull wire beads 220a, 220b.

In block 1032, the method can include connecting the proximal pull wire 140a and the distal pull wire 140b with a suture linkage 224. The suture linkage can include a proximal suture knot 222a that can be attached to a distal end of a proximal pull wire 140a and a distal suture knot 222b that can be attached to a proximal end of a distal pull wire 140b.

In block 1036, the method can include extending a loop opening 405 through a locking portion 18 of an implantable medical device 12. In block 1040 the method can include extending a distal end of the distal pull wire 140b through the loop opening 405. In block 1044, the method can include preventing proximal translation of the distal pull wire 140b as the proximal pull wire is translated proximally with respect to the distal pull wire 140b due to the pull wire slack 226 of the suture linkage 224. In block 1048, the method can include facilitating proximal translation of the distal pull wire 140b in response to the proximal pull wire 140a being translated by more than a predetermined length of the pull wire slack 226.

According to some embodiments, the method can include preventing premature deployment of the implantable medical device 12 due to the pull wire slack 226 of the suture linkage 224. In some embodiments, the method can include moving the loop wire 400 and the distal pull wire 140b to release the implantable medical device 12 from the delivery system 10a, 10b.

According to some embodiments, the method can include, following proximal translation of the proximal pull wire 140a by more than the predetermined length L1 of the pull wire slack 226, causing the distal suture knot 222b to abut the distal pull wire bead 220b. Once distal suture knot 222b engages distal pull wire bead 220b, the distal pull wire 140b and the proximal pull wire 104a can translate proximally as a unit.

In some embodiments, constructing the tubular body 90 can include joining a flexible coil 200a between a proximal hypotube 100 and a compressed distal portion 300 such that the lumen 608 extends from a proximal end 102 of the proximal hypotube 100, through the proximal hypotube 100, through the flexible coil 200a, through the compressed distal portion 300, and to a distal end 304 of the compressed distal portion 300. Flexible coil can be inhibited from elongating from the construction of tubular body 90.

In some embodiments, upon initial proximal translation of the proximal pull wire 140a, the distal pull wire 140b remains fixed in position while the distal suture knot 222b slides along the distal pull wire 140b for the predetermined length L1 of the pull wire slack 226. In some embodiments, the method can include translating the proximal pull wire 140a proximally for a distance longer than the predetermined length L1 to thereby deploy the implantable medical device 12.

The descriptions contained herein are examples of embodiments of the invention and are not intended in any way to limit the scope of the invention. As described herein, the invention contemplates many variations and modifications of the implantation system and associated methods, including alternative geometries of system components, alternative materials, additional or alternative method steps, etc. Modifications apparent to those skilled in the pertinent art are intended to be within the scope of the claims which follow.

The invention claimed is:

1. A delivery system for deploying an implantable medical device to a target location of a body vessel, the delivery system comprising:
  a tubular body comprising a lumen extending therethrough and a compressed distal portion;
  a loop wire comprising a first end affixed to the tubular body and comprising a loop opening positioned approximate the compressed distal portion;
  a pull wire extending through the lumen, the pull wire comprising
    a proximal pull wire portion;
    a distal pull wire portion, separate from the proximal pull wire portion; and
    a suture linkage connecting the proximal pull wire portion and the distal pull wire portion,
    the suture linkage comprising:
      a proximal suture knot slideably engaged to the proximal pull wire portion; and
      a distal suture knot slideably engaged to the distal pull wire portion.

2. The delivery system of claim 1, wherein:
  a distal end of the proximal pull wire portion comprises a proximal pull wire bead and a proximal end of the distal pull wire portion comprises a distal pull wire bead,
  the proximal pull wire bead is configured to retain the proximal suture knot on the proximal pull wire portion during proximal translation of the proximal pull wire portion and the distal pull wire bead is configured to retain the distal suture knot on the distal pull wire portion during proximal translation of the distal pull wire portion, the loop wire and the distal pull wire portion are positioned to secure the implantable medical device to the delivery system;
  the suture linkage comprises pull wire slack that facilitates the proximal pull wire portion to be translated proximally with respect to the distal pull wire portion while the distal pull wire portion remains stationary for a predetermined length causing the distal suture knot to translate proximally to abut the distal pull wire bead such that when the distal suture knot abuts the distal pull wire bead both the proximal pull wire portion and distal pull wire portion translate proximally as a unit; and
  the pull wire slack is effective to inhibit premature deployment of the implantable medical device.

3. The delivery system of claim 2, wherein the predetermined length of the pull wire slack comprises a length between approximately 2 mm and 3 mm.

4. The delivery system of claim 2, wherein the suture linkage has a predetermined length that fits within the tubular body of the delivery system.

5. The delivery system of claim 2, wherein upon initial proximal translation of the proximal pull wire portion, the distal pull wire portion remains fixed in position while the distal suture knot slides along the distal pull wire portion for the predetermined length of the pull wire slack.

6. The delivery system of claim 2, wherein the proximal pull wire portion is translated proximally for a distance longer than the predetermined length to deploy the implantable medical device.

7. The delivery system of claim 2, wherein the proximal pull wire bead comprises a first laser weld forming a diameter larger than a diameter of the proximal suture knot and the distal pull wire bead comprises a second laser weld forming a diameter larger than a diameter of the distal suture knot.

8. The delivery system of claim 1, wherein the loop wire and the pull wire are movable to release the implantable medical device from the delivery system.

9. The delivery system of claim 1, wherein the tubular body further comprises:
  a proximal hypotube;
  a flexible coil extending from a distal end of the proximal hypotube;
  the compressed distal portion extending from a distal end of the flexible coil; and
  wherein the lumen extends from a proximal end of the proximal hypotube, through the proximal hypotube, through the flexible coil, through the compressed distal portion, and to a distal end of the of the compressed distal portion.

10. The delivery system of claim 9, further comprising a sleeve that extends along a majority of the of the flexible coil.

11. The delivery system of claim 1, wherein each suture knot comprises a clove knot adapted to slide against the pull wire when the pull wire is translated proximally.

12. The delivery system of claim 1, wherein the distal suture knot and the proximal suture knot each comprise a clove hitch knot.

13. A method comprising:
  providing a tubular body comprising a lumen extending therethrough and a compressed distal portion;
  affixing a loop wire to the tubular body;
  compressing the compressed distal portion;
  positioning a loop opening in the loop wire approximate a distal end of the compressed distal portion while the loop wire is affixed to the tubular body such that the loop wire is extended through the lumen;

extending a distal pull wire portion through a distal portion of the lumen of the tubular body;

extending a proximal pull wire portion, separate from the distal pull wire portion, through a proximal portion of the lumen of the tubular body;

connecting the proximal pull wire portion and the distal pull wire portion with a suture linkage, the suture linkage comprising a proximal suture knot attached to the proximal pull wire portion and a distal suture knot attached to the distal pull wire portion, the proximal pull wire portion, suture linkage, and distal pull wire portion thereby forming a pull wire;

extending the loop opening through a locking portion of an implantable medical device; and extending a distal end of the distal pull wire portion through the loop opening.

14. The method of claim 13, further comprising:

preventing proximal translation of the distal pull wire portion as the proximal pull wire portion is translated proximally with respect to the distal pull wire portion due to pull wire slack of the suture linkage;

facilitating proximal translation of the distal pull wire portion in response to the proximal pull wire portion being translated proximally by more than a predetermined length of the pull wire slack.

15. The method of claim 14, further comprising:

welding a proximal pull wire bead on a distal end of the proximal pull wire portion and a distal pull wire bead on a proximal end of the distal pull wire portion; and following proximal translation of the proximal pull wire portion by more than the predetermined length of the pull wire slack, causing the distal suture knot to abut the distal pull wire bead thereby causing the distal pull wire portion and the proximal pull wire portion to translate proximally as a unit.

16. The method of claim 14, wherein upon initial proximal translation of the proximal pull wire portion, the distal pull wire portion remains fixed in position while the distal suture knot slides along the distal pull wire portion for the predetermined length of the pull wire slack.

17. The method of claim 14, further comprising:

translating the proximal pull wire portion proximally for a distance longer than the predetermined length, thereby deploying the implantable medical device.

18. The method of claim 13, further comprising:

preventing premature deployment of the implantable medical device due to pull wire slack of the suture linkage.

19. The method of claim 13, further comprising:

moving the loop wire and the distal pull wire portion to release the implantable medical device from the tubular body.

20. The method of claim 13, further comprising:

constructing the tubular body by joining a flexible coil between a proximal hypotube and a distal hypotube comprising the compressed distal portion such that the lumen extends from a proximal end of the proximal hypotube, through the proximal hypotube, through the flexible coil, through the compressed distal portion, and to a distal end of the of the compressed distal portion and such that the flexible coil is inhibited from elongating.

* * * * *